(12) United States Patent
Stuke

(10) Patent No.: US 10,360,670 B2
(45) Date of Patent: Jul. 23, 2019

(54) METHOD FOR THE NON-DESTRUCTIVE TESTING OF THE VOLUME OF A TEST OBJECT AND TESTING DEVICE CONFIGURED FOR CARRYING OUT SUCH A METHOD

(71) Applicant: GE Sensing & Inspection Technologies GmbH, Hurth (DE)

(72) Inventor: Ingo Stuke, Schlesswig Holstein (DE)

(73) Assignee: GE Sensing & Inspection Technologies GmbH, Hurth (DE)

( * ) Notice: Subject to any disclaimer, the term of this patent is extended or adjusted under 35 U.S.C. 154(b) by 0 days.

(21) Appl. No.: 14/765,757

(22) PCT Filed: Feb. 3, 2014

(86) PCT No.: PCT/EP2014/052033
§ 371 (c)(1),
(2) Date: Aug. 4, 2015

(87) PCT Pub. No.: WO2014/118367
PCT Pub. Date: Aug. 7, 2014

(65) Prior Publication Data
US 2017/0330314 A1    Nov. 16, 2017

(30) Foreign Application Priority Data
Feb. 4, 2013   (DE) .................. 10 2013 001 808

(51) Int. Cl.
*G06T 7/00* (2017.01)
*G06T 7/33* (2017.01)
(Continued)

(52) U.S. Cl.
CPC ............... *G06T 7/001* (2013.01); *G01B 7/00* (2013.01); *G01B 15/00* (2013.01); *G01B 17/00* (2013.01);
(Continued)

(58) Field of Classification Search
CPC .. G06T 7/00; G06T 7/337; G01B 7/00; G01B 15/00; G01B 17/00
See application file for complete search history.

(56) References Cited

U.S. PATENT DOCUMENTS 4,803,639 A    2/1989   Steele et al.
5,848,115 A    12/1998  Little et al.
(Continued)

OTHER PUBLICATIONS

Sikora et al: "Application of digital radiography in evaluation of crack propagation rate in cast steel specimens", AFE, 2009.*
(Continued)

*Primary Examiner* — Ruiping Li
(74) *Attorney, Agent, or Firm* — Mintz Levin Cohn Ferris Glovsky and Popeo, P.C.

(57) ABSTRACT

A method for the non-destructive testing of the volume of a test object, during the course of which a volume raw image of the test object is recorded by a suitable non-destructive imaging testing method. Then, those regions of the volume raw image are identified that are not to be attributed to the test object material. It is checked whether an identified region is completely embedded in regions that are to be associated with the test object material. If necessary, such a region is assimilated to those regions that are to be associated with the test object material, forming a filled volume raw image. Finally, a difference is generated between the volume raw image and the filled volume raw image, forming a first flaw image.

20 Claims, 3 Drawing Sheets

(51) Int. Cl.
| | |
|---|---|
| *G01B 7/00* | (2006.01) |
| *G01B 15/00* | (2006.01) |
| *G01B 17/00* | (2006.01) |
| *G01N 23/046* | (2018.01) |
| *G01N 27/90* | (2006.01) |
| *G01N 29/06* | (2006.01) |
| *G06K 9/62* | (2006.01) |
| *G06T 5/50* | (2006.01) |

(52) U.S. Cl.
CPC ....... *G01N 23/046* (2013.01); *G01N 27/9073* (2013.01); *G01N 29/069* (2013.01); *G01N 29/0672* (2013.01); *G06K 9/6267* (2013.01); *G06T 5/50* (2013.01); *G06T 7/337* (2017.01); *G06T 2207/10072* (2013.01); *G06T 2207/20221* (2013.01); *G06T 2207/20224* (2013.01); *G06T 2207/30116* (2013.01); *G06T 2207/30164* (2013.01)

(56) References Cited

U.S. PATENT DOCUMENTS

| | | | |
|---|---|---|---|
| 6,229,872 B1 * | 5/2001 | Amos | G01N 23/00 356/237.1 |
| 6,341,153 B1 | 1/2002 | Rivera et al. | |
| 6,748,112 B1 | 6/2004 | Nguyen et al. | |
| 6,839,457 B1 | 1/2005 | Azuma et al. | |
| 2009/0034828 A1 | 2/2009 | Ferro et al. | |
| 2010/0220910 A1 | 9/2010 | Kaucic et al. | |
| 2010/0235153 A1 | 9/2010 | Sharp et al. | |
| 2010/0278440 A1 | 11/2010 | Dragovich et al. | |

OTHER PUBLICATIONS

International Search Report and Written Opinion dated May 26, 2014 which was issued in connection with PCT Patent Application No. PCT/2014/05233 which was filed on Feb. 3, 2014.

Zhou et. al. : "Research on Automatic Inspection Techniques of Real-Time Radiography for Turbine-Blade", Chinese Journal of Mechanical Engineering, 2005.

Liu Jing et. al.: "A Study of Registration Method between Hollow Turbine Blades CAD Model and CT Slice Model", Computer Engineering and Applications, 2003.

Liu Jing et. al.: "Registration of the Reconstructed CT Slice Model and CAD Model Based on the SVD-ICP Algorithm", Computer Engineering and Applications 2004.

Liang Xinhe et. al.: "A rapid inspection method for Large Water Turbine Blade", International Conference on Mechatronics and Automation (ICMA 2010), pp. 712-716 Location: Xi'an, People's Republic of China Aug. 4-7, 2010.

Herold et al., "A Third Generation Automatic Defect Recognition System", Hamburg University of Technology, XP055321775, Aug. 30, 2004.

Hadwiger et al., "Interactive Volume Exploration for Feature Detection and Quantification in Industrial CT Data", IEEE Transactions on Visualisation and Computer Graphics, vol. No. 14, Issue No. 6, pp. 1507-1514, Nov./ Dec. 2008.

A European Office Action issued in connection with corresponding EP Application No. 14703053.0 on Dec. 2, 2016.

* cited by examiner

US 10,360,670 B2

METHOD FOR THE NON-DESTRUCTIVE TESTING OF THE VOLUME OF A TEST OBJECT AND TESTING DEVICE CONFIGURED FOR CARRYING OUT SUCH A METHOD

FIELD OF THE INVENTION

Embodiments of the present invention relate to the field of the automated non-destructive testing of the volume of a test object by means of suitable testing methods, such as ultrasonic testing, eddy current testing or X-ray testing. An embodiment relates to a method for the non-destructive testing of the volume of a test object as well as to a testing device configured for carrying out such a method. In particular, a three-dimensional image of the test object can be formed by means of the method according to an embodiment of the invention, in which detected flaw indicators are registered that can be associated with the test object volume. The three-dimensional image can be the starting point of further method steps for flaw analysis and possibly flaw classification. In an embodiment, in an at least partially, and in an embodiment fully, automated manner a classification of the examined test object as "In order"/"Not in order" in accordance with predefined classification parameters is offered. Moreover, the method according to an embodiment can be designed to be adaptive in order to adapt in a self-learning manner to changed testing parameters.

BACKGROUND

A multitude of testing methods is known in the field of non-destructive material testing that are based on a comparison of test data, which were obtained on a test object by means of a non-destructive testing method, with a CAD model of the test object. Due to the required CAD model of the test object, these testing methods can only be applied in an economical manner to test objects of which a larger number of identical specimens are to be tested, e.g. within the context of series production. Furthermore, an alignment of the actual test data to the CAD model is necessary (a "registration"), which requires great computing power.

SUMMARY OF INVENTION

Embodiments of the present invention propose a method for the non-destructive testing of the volume of a test object which is suitable for real-time testing of, for example, series-produced parts. Embodiments of the present invention propose a testing device suitable for carrying out such a method.

Embodiments of the present invention provide a method and a testing device. The features of the dependent claims, and of the described embodiments, can be combined with one another within the context of what is technically feasible, even if this is not explicitly described hereinafter. This also applies to a combination of method and device claims.

In an embodiment, the method and the testing device are based upon the formation of volume raw images of a test object by means of X-ray computer tomography. Recording three-dimensional X-ray tomography images inline, e.g. within a production line, has become possible at the time of the filing of this application thanks to CT scanners working fully automatically that are fed test objects in an automated manner. In particular, an embodiment relates to analyzing, also inline, more particularly in real time, the volume raw images of the scanned test objects produced e.g. in such a CT method and make them usable for flaw or test object classification.

A method according to an embodiment comprises at least the following method steps:

a. recording a volume raw image of the test object by means of a suitable non-destructive imaging testing method, such as X-ray computer tomography, b. identifying the regions of the volume raw image that are not to be attributed to the test object material (hereinafter "dark regions"), e.g. by means of gray-value acquisition and threshold value analysis, c. checking the identified dark region as to whether it is completely embedded in regions that are to be associated with the test object material (hereinafter "light regions"), and, if necessary, assimilating such a dark region to the surrounding light regions, forming a filled volume raw image or a data set on which that is based, and d. generating the difference between the volume raw image and the filled volume raw image, forming a first flaw image or a data set on which that is based.

All of the images formed within the context of the method constitute graphic representations of data sets that include the test object volume completely or at least partially. The image processing steps discussed above are therefore typically carried out with the underlying data sets. The graphic representations primarily serve for illustrating the test result to a human operator of a testing device configured according to an embodiment of the invention. Hereinafter, the terms "image" or "graphic representation" on the one hand, and "data set" on the other hand, are used substantially synonymously.

In an embodiment, the method for forming a first flaw image can be carried out in a fully automated manner and provides a reliable detection of flaw indications caused by larger flaws, such as inclusions of air, piping etc. in the test object volume. The detected flaws can then be subjected to a partially, or in an embodiment fully, automated flaw classification by means of suitable methods, such as threshold analyses etc, or serve as starting points ("seed points") for the "region-growing" method known from the prior art, or for its development according to the paper "Interactive Volume Exploration for Feature Detection and Quantification in Industrial CT Data" by Markus Hadwiger et al. in IEEE Transactions on Visualisation and Computer Graphics, Vol. 14, No. 6 (November/December 2008), 1507-1514.

In an embodiment, the volume raw image is additionally processed as follows:

e. applying a filter algorithm, such as a cutoff filter or median filter, for amplifying possible flaw indicators, forming a filtered volume raw image, and f. limit value generation of the filtered volume raw image, forming a second flaw image or a data set on which that is based.

This development forms a second flaw image which also contains flaw indications of flaws that only produce weaker signals in the volume raw image, for example due to their small size or also due to a density that is only slightly different locally, so that possibly they are not contained in the first flaw image according to embodiments of the present invention. In particular, it is possible, in connection with forming the filtered volume raw image, to also carry out a subtraction of the volume raw image in addition to the application of suitable filter algorithms.

In an embodiment, the first flaw image and the second flaw image are merged into a combined flaw image or a data set on which that is based.

In an embodiment, in the combined flaw image, those regions are suppressed that are not associated with the test object material in the volume raw image, for example due to their local gray value. Thus, flaw indications that are not attributable to the test object, but are, for example, artifacts of the image-forming testing method, can be reliably suppressed. On the one hand, this results in an improved interpretability of the graphic representation of the result of the method according to embodiments of the present invention, on the other hand, this offers advantages in a subsequent flaw detection and classification carried out in a partially or fully automated manner.

In addition to the X-ray computer tomography already mentioned, the non-destructive imaging testing method can also be a tomography method based on ultrasound or eddy currents.

The method is particularly suitable for testing series-produced workpieces, e.g. within the context of an inline real time inspection.

an embodiment permits the suppression of supposed flaw indications that are actually not correlated to structures of a series-produced test object that are to be considered flawed. Such flaw indications can be, for example, artifacts of the testing method used for image forming. In X-ray tomography, reflections on (inner) boundary surfaces of the test object are observed, for example, which can lead to local shading. The attenuation of the X-radiation in the test object material also results—at least in test objects having a larger volume or consisting of highly absorbing materials—in a drop in the X-ray intensity towards the center of the test object. But also production-related faults, which, for example in casting processes, can often occur always at the same positions and which can be counteracted by means of, for example, a suitable local dimensioning of the test object, can constitute such flaw indications that one would like to disregard in a flaw assessment. For this purpose, the method according to an embodiment is developed by means of the following additional method steps:

g. forming a volume reference image from volume raw images of one or more test object(s) which was/were classified to be "In order" on the basis of predefined test criteria, h. generating the difference between, on the one hand, one of the first flaw image, the second flaw image or the combined flaw image and, on the other hand, the volume reference image.

Naturally, the volume reference image contains information on the above-mentioned structures that are to be suppressed. A subtraction of this volume reference image from the first, second or combined flaw image therefore specifically eliminates these undesired structures. In an embodiment, the method further comprises a registration step in which a registration of a volume raw image to a volume reference image or to a 3D CAD model of the test object takes place. Alternatively, or also additionally, the method can also comprise a registration of the volume reference image to a 3D CAD model of the test object. In an embodiment, a registration takes place of both the volume raw image as well as the volume reference image to a 3D CAD model of the test object.

Other embodiments of the method according to the invention are explained in the context of the exemplary embodiments, which are to be understood to be examples and non-limiting. In particular, this means that the method-related features disclosed there can be combined, within the context of what is technically possible, with individual or several of the features discussed above as well as with the embodiments or developments.

Embodiments of the device according to the invention are discussed below in a cursory manner. With regard to the mode of operation as well as to the advantageous effects of the device in its various disclosed embodiments as well as to the comprised features, reference is made to the above discussion of the method according to the embodiments of the invention, which can be directly transferred to the equivalent device features.

If a device according to embodiments of the present invention is suitable for recording and processing three-dimensional images of a test object and possibly comprises components for this purpose, which are separately designated in the following, these components can be realized as software-based parts of a computer-based system. The computer-based system can be a commercially available, operating system-based PC system suitable for running freely programmed application programs. Alternatively, the individual components can also be designed as microcode for freely programmable microprocessors, or also as hardware-implemented component members. Particularly in the case of computationally intensive operations, the latter can have advantages with regard to speed.

A testing device according to embodiments of the present invention for the non-destructive testing of the volume of a test object comprises at least the following features:

a. an image forming unit for recording a volume raw image of the test object by means of a suitable non-destructive imaging testing method, b. an image processing unit for the further processing of a volume raw image which is configured to:

i. identify regions of the volume raw image that are not to be attributed to the test object material, ii. check an identified region as to whether it is completely embedded in regions that are to be associated with the test object material, and, if necessary, assimilate this region to those regions that are to be associated with the test object material, forming a filled volume raw image, and iii. forming a first flaw image while generating the difference between the volume raw image and the filled volume raw image.

In this case, the image forming unit can, in particular, be configured to form volume raw images of a test object by means of a tomography method based on X-radiation, ultrasound or eddy currents. In particular, it can be configured to carry out an inline inspection of series-produced components, for which purpose it has a largely or fully automated manipulator unit for feeding the test objects to the image forming unit. In particular, the image forming unit can be an X-ray computer tomograph configured for forming three-dimensional test objects.

In an embodiment, the image processing unit is configured to further process the volume raw image as follows:

c. applying a filter algorithm, such as a cutoff filter or median filter, for amplifying possible flaw indicators, forming a filtered volume raw image, and d. limit value generation of the filtered volume raw image, forming a second flaw image.

In another embodiment, the image processing unit is configured to merge the first flaw image and the second flaw image into a combined flaw image.

Generally, the testing device can comprise a display unit on which the formed flaw images can be displayed to an operator.

In another embodiment, the image processing unit of the testing device is configured to suppress in the combined flaw image those regions that are not to be associated with the test object material in the volume raw image.

Moreover, the image processing unit can be configured to carry out a subtraction of the volume raw image in order to form the filtered volume raw image.

In another embodiment, the testing device according to the invention moreover comprises a classification unit configured to classify a test object as being "In order"/"Not in order" on the basis of predefined test criteria. Such a classification can be made, for example, by means of a partially or fully automated inspection of flaw indications in the first, second or combined flaw images formed according to an embodiment of the invention. If necessary, an additional intervention by the user can also be provided.

In an embodiment, the image processing unit of the testing device is furthermore configured to:

e. form a volume reference image from volume raw images of one or more test object(s) which was/were classified to be "In order" on the basis of predefined test criteria, and f. generate the difference between, on the one hand, the first flaw image, the second flaw image or the combined flaw image and, on the other hand, the volume reference image.

In an embodiment, the testing device further comprises a registration unit configured to carry out at least one of the two following registration steps:

g. registration of a volume raw image to a volume reference image or to a 3D model of the test object, or h. registration of the volume reference image to a 3D model of the test object.

BRIEF DESCRIPTION OF THE DRAWINGS

Other advantages and features of the various embodiments of the testing device according to the invention are also apparent from the following exemplary embodiments. It is pointed out that the method features discussed there can be directly transferred to the device according to the invention to the extent it is characterized, within the context of the present invention, as carrying out certain process steps.

The exemplary embodiments will be explained with reference to the drawing, in which the Figures show the following.

DETAILED DESCRIPTION

Figure 1:
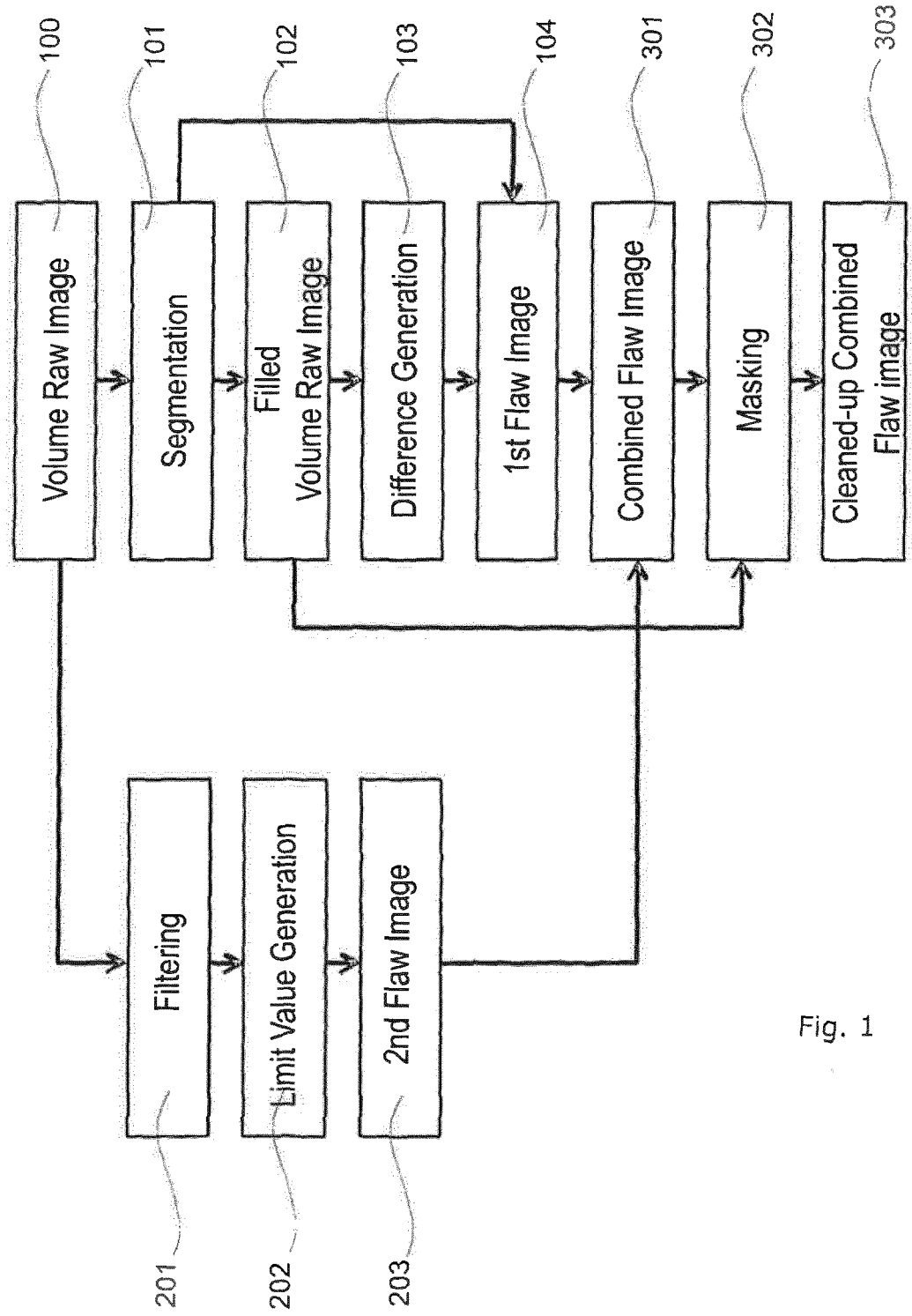
FIG. 1 is a first exemplary embodiment of a method according to the invention.

FIG. 1 schematically shows the process flow of an embodiment of a method according to the invention. In this embodiment, the method is applied to a three-dimensional volume raw image obtained by means of X-ray computer tomography on a pump housing formed as a casting. The starting point of the method is in Block 100 a three-dimensional volume raw image of the pump housing. This is subjected in Block 101 to a method step which is referred to in the context of the present invention as segmentation. During segmentation, those regions of the volume raw image are identified that are not to be attributed to the test object material. The basis for such an association can be, for example, an analysis of the gray values in the volume raw image including a threshold analysis.

However, the problem with an association made in this manner is that larger faults, piping or included gas bubbles in the test object, for example, locally cause a gray value in the volume raw image that matches the gray value of the air surrounding the test object. In the case of these flaw regions, there is therefore the danger that they are not attributed to the test object volume. In the segmentation step, the volume raw image is therefore analyzed in order to identify those regions in the volume raw image that are not to be attributed to the test object material. In a subsequent processing step, the regions of the volume raw image identified herein are checked as to whether they are completely embedded in regions that are to be associated with the test object material. In a process step subsequent thereto, the identified regions that are completely embedded in the test object material are assimilated to those regions that are to be associated with the test object material, for example, by associating a medium gray value of the test object volume with them. By assimilating the identified regions to the surrounding regions to be associated with the test object material, a filled volume raw image is formed in step 102.

In the subsequent method step in Block 103, a difference is generated between the volume raw image according to Block 100 and the filled volume raw image according to Block 102, and results in a first flaw image from which first flaw indications are apparent.

At the same time, the volume raw image from Block 100 is subjected to further processing steps in a second branch of the method. In Block 201, the volume raw image is filtered, for example by means of a cutoff filter or median filter. In the subsequent processing step 202, a difference is generated between the volume raw image from Block 100 and the filtered volume raw image from Block 201. Subsequent thereto, in process step 203, a limit value is generated of the filtered difference image from block 202, whereby flaw indications that do not exceed a predefined level are blanked out. Second flaw indications, which are correlated to smaller flaws in the test object material, remain. The sensitivity of the method according to an embodiment of the invention can be influenced to a substantial extent by the selection of the threshold used here. In Block 204, a second flaw image is provided as a result of this second processing branch.

Then, the first flaw image (Block 104) from the first processing branch and the second flaw image (Block 203) from the second processing branch are merged into a combined flaw image, which takes place in step 301.

In the subsequent masking step according to Block 302, those regions of the flaw image are masked in the combined flaw image according to Block 301 that are not to be attributed to the test object volume. Here, the filled volume raw image from Block 102 can be used. It is possible to extract from the filled volume raw image, e.g. by means of threshold analysis, which image regions are to be attributed to the test object volume. By means of this masking step, all flaw indications are eliminated that are outside the test object, which therefore must be artifacts. The result of this masking step is a cleaned-up combined flaw image in Block 303, which can then be subjected to subsequent processing steps, for example for a partially or fully automated flaw detection and classification.

Figure 2:
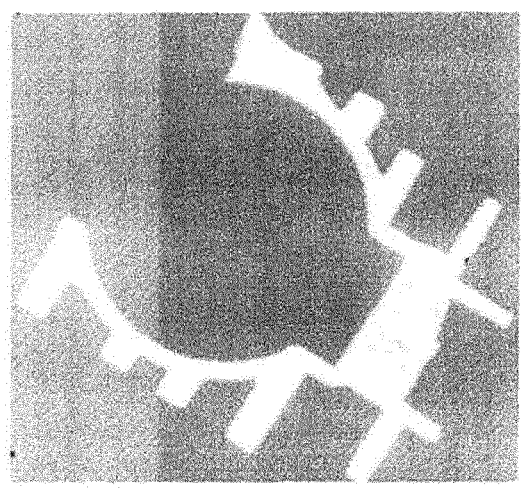
FIG. 2 is an exemplary section through a test object's volume raw image to be processed.

FIG. 2 shows a sectional view through the test object, which was obtained by means of a volume raw image according to Block 100 serving as the starting point of the method according to an embodiment of the invention.

Figure 3:
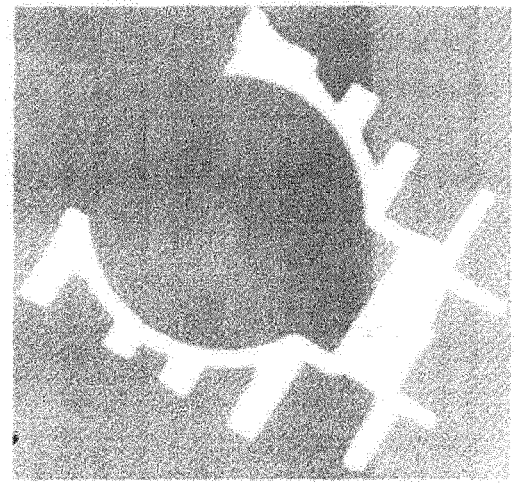
FIG. 3 is a section through a cleaned-up combined flaw image of the test object obtained according to an embodiment of the invention, with the section shown corresponding to the section from FIG. 2.

FIG. 3 now shows an equivalent sectional view of the same test object that was obtained on the cleaned-up combined flaw image according to Block 303, which is the result of the method according to an embodiment of the invention. It is very clear that the number of the flaw indications apparent from the sectional view is considerably increased in FIG. 3 compared to FIG. 2. At the same time, all regions of the image situated within the outline of the test object are associated with the test object material, so that all flaw indications in FIG. 3 can be subjected to further automated processing. Therefore, the method according to an embodiment of the invention permits reliably avoiding such flaws that are caused by flaw indications above a certain size no longer being attributed to the test object material.

Figure 4:
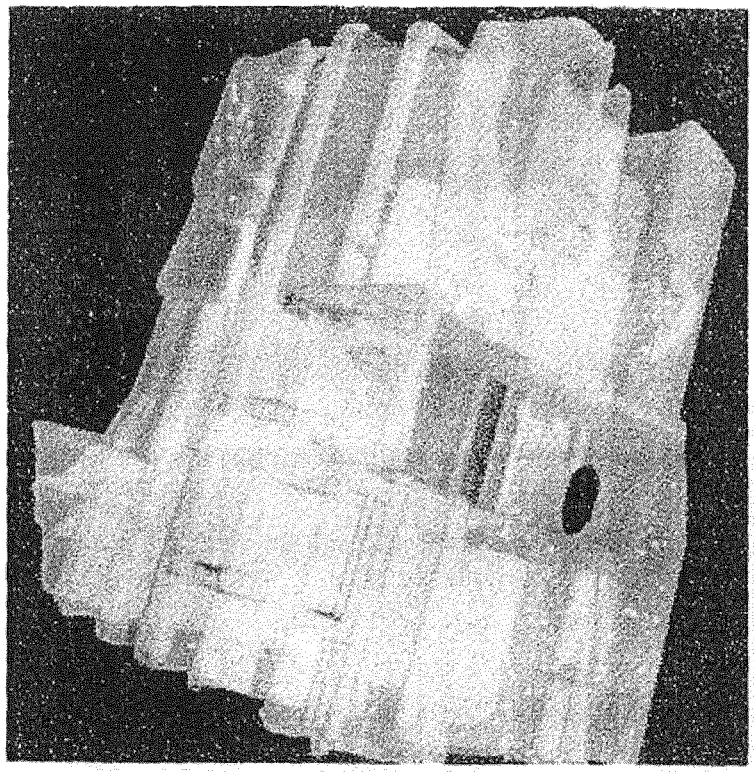
FIG. 4 is a cleaned-up combined three-dimensional flaw image of the test object obtained according to an embodiment of the invention, according to FIG. 2.

FIG. 4 now shows a perspective view of a combined flaw image of the pump housing, of which FIGS. 2 and 3 show sectional views. The illustration according to FIG. 4 and the underlying data were obtained by a superposition of the cleaned-up combined flaw image according to Block 303, which was obtained according to an embodiment of the invention, with the filled volume raw image according to Block 102, which was also obtained during the course of the method according to an embodiment of the invention. On the one hand, the structure of the examined test object is clearly apparent from this combined illustration, on the other hand, the flaw indications are easily recognizable to an operator of a testing system configured according to an embodiment of the invention. Furthermore, in the data set which is the basis of the illustration according to FIG. 4, the flaw indications can very easily be subjected to an automated inspection and classification.

Figure 5:
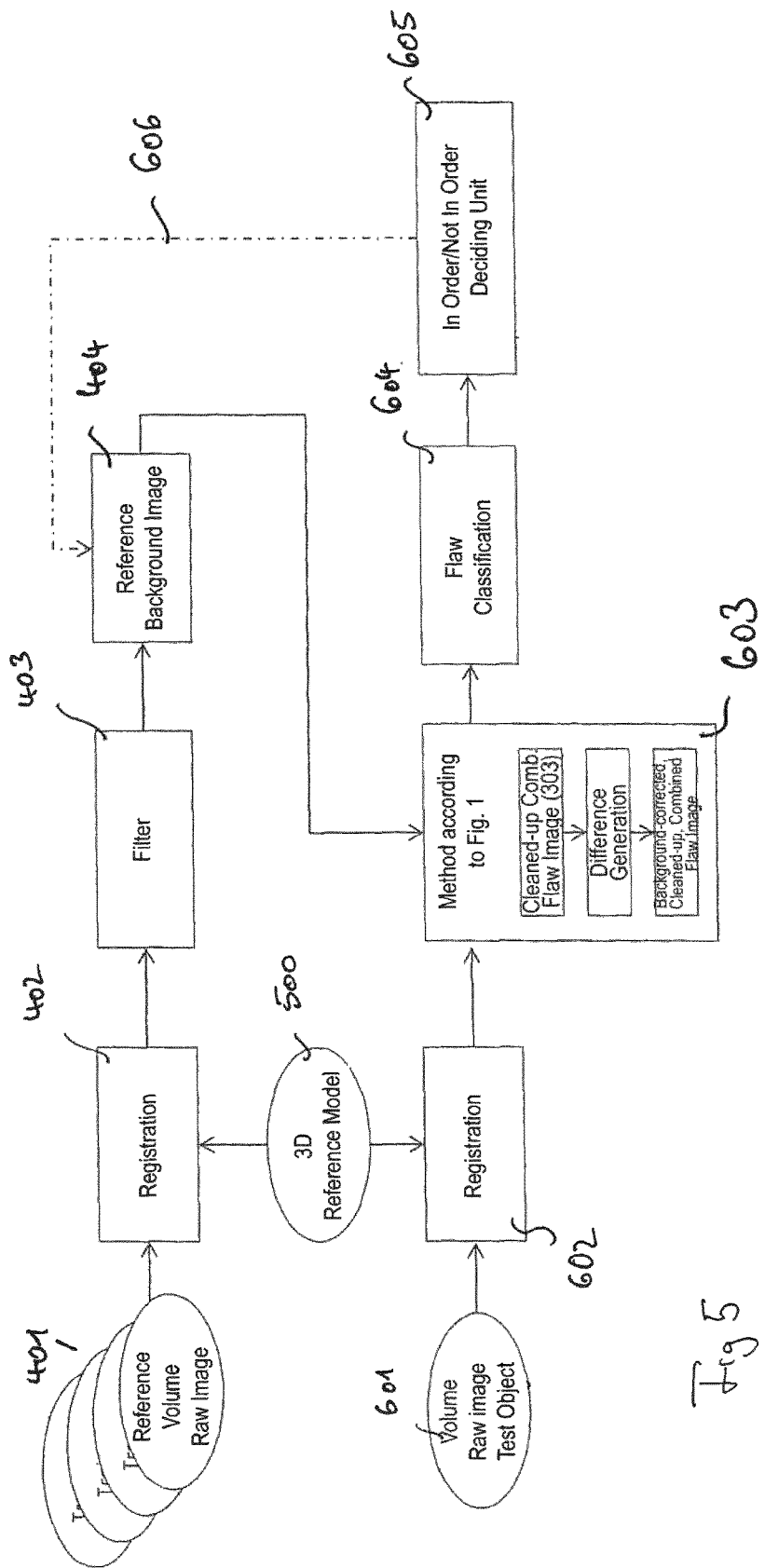
FIG. 5 is a schematic view of a method according to an embodiment of the invention.

FIG. 5 shows an embodiment of the method according to the invention, which comprises the method according to FIG. 1. This embodiment permits the effective suppression of artifacts in a volume raw image of a test object that were caused by the non-destructive image forming testing method used. A requirement in order for the developed method to be capable of being carried out is that reference volume raw images are provided of a plurality of test objects, which were inspected, for example, by means of other non-destructive testing methods and which where classified as being "In order" within the context of the testing task to be carried out. This plurality of reference volume raw images is registered in step 402 to a reference model, for example a three-dimensional CAD model of a test object. Within the context of the present invention, registration means that the volume raw images obtained from actual test objects are aligned to a reference model of the test object. This registration is essential for the developed method to succeed, because here, volume raw images are to be compared with each other that were obtained on different test objects, which did not inevitably had to have the same orientation in space during the recording of the reference volume images, due to the testing method used. The result of the registration step 402 is a plurality of registered, i.e. aligned to a reference model, reference volume raw images of different test objects that were classified as being "In order".

In the subsequent processing step 403, the registered reference volume raw images, if necessary, are subjected to a suitable filtering, such as, again, a cutoff filter or median filter, in order to have structures that possibly exist come out more clearly.

In the subsequent processing step 404, an averaging process is carried out over the plurality of the registered, optionally filtered, reference volume raw images in order to form an adaptive reference background image.

In step 601, a volume raw image of a test object to be classified is recorded by means of a non-destructive imaging testing method, which matches the image-forming testing method used for recording the reference images in step 401. In the subsequent step 602, the recorded volume raw image of the test object to be classified is aligned in a registration step in Block 602 to the reference model according to Block 500. The aligned volume raw image formed here of the test object to be classified is then subjected in Block 603 to the method according to FIG. 1. However, a difference is still generated here between the result of the method according to FIG. 1, i.e. between the cleaned-up combined flaw image according to Block 303, and the registered flaw reference image formed in step 404. In addition, a threshold analysis can be carried out on the formed difference image in order to suppress smaller deviations from the reference image. Also in this case, the result of the method according to an embodiment of the invention can be influenced decisively by the suitable selection of the threshold. The background-corrected, cleaned-up, combined flaw image resulting in Block 603 can then be subjected in Block 604 to a flaw classification, which may proceed, in particular, in a partially or fully automated manner. Using the result of this flaw classification in Block 604, a deciding unit can classify the analyzed test object as being "In order"/"Not in order" in Block 605. On the one hand, this classification can take place fully automatically, on the other hand, an intervention by an operator is also conceivable in this case.

Another embodiment of the method according to the invention provides that the volume raw image that was obtained on a test object analyzed by means of the method discussed above and classified as being "In order" in Block 605 is added to the set of the reference volume raw images according to step 401. A self-learning system is thus developed in which slowly changing influences, such as minor geometry changes of the analyzed castings within the series due to ageing phenomena of the molds used, or changed bubble inclusions, can be automatically compensated by slightly changed process parameters in casting processes.

Whilst exemplary and embodiments of the invention have been described herein, the skilled person will appreciate that other embodiments are possible and contemplated. The invention is intended to encompass all such embodiments that fall within the scope of the appended claims.

The invention claimed is:

1. A method for the non-destructive testing of a volume of a test object, the method comprising:

recording a three-dimensional volume raw image of the test object by a non-destructive imaging testing method;

identifying regions of the three-dimensional volume raw image that are not to be attributed to the test object material by a threshold analysis of pixel values in the three-dimensional volume raw image;

checking an identified region of the three-dimensional volume raw image to determine whether it is completely embedded in regions that are to be associated with the test object material;

assimilating the identified region of the three-dimensional volume raw image to the regions of the three-dimensional volume raw image that are to be associated with the test object material when the identified region is determined to be completely embedded in the regions that are to be associated with the test object material, thereby forming a filled three-dimensional volume raw image; and generating the difference between the three-dimensional volume raw image and the filled three-dimensional volume raw image, forming a first three-dimensional flaw image.

2. The method according to claim 1, further comprising:
applying a filter algorithm to the three-dimensional volume raw image for amplifying possible flaw indicators, forming a filtered three-dimensional volume raw image; and limit value generation of the filtered three-dimensional volume raw image, forming a second three-dimensional flaw image.

3. The method according to claim 2, wherein the first three-dimensional flaw image and the second three-dimensional flaw image are merged into a combined three-dimensional flaw image.

4. The method according to claim 3, wherein, in the combined three-dimensional flaw image, the regions that are not associated with the test object material are suppressed in the filled three-dimensional volume raw image.

5. The method according to claim 1, wherein a subtraction of the three-dimensional volume raw image is carried out for forming the filtered three-dimensional volume raw image.

6. The method according to claim 1, wherein the non-destructive imaging testing method is a tomography method based on X-radiation, ultrasound, or eddy currents.

7. The method according to claim 1, wherein the test object is a series-produced workpiece.

8. The method according to claim 3, further comprising:
forming a three-dimensional volume reference image from three-dimensional volume raw images of one or more test object(s) which was/were classified on the basis of predefined test criteria; and generating the difference between, on the one hand, the first three-dimensional flaw image, the second three-dimensional flaw image, or the combined three-dimensional flaw image and, on the other hand, the three-dimensional volume reference image.

9. The method according to claim 8, further comprising registering a three-dimensional volume raw image to a three-dimensional volume reference image or to a 3D model of the test object.

10. The method according to claim 9, further comprising registering the three-dimensional volume reference image to the 3D model of the test object.

11. A testing device for a non-destructive testing of a volume of a test object, the testing device comprising:
an image forming unit configured to record a three-dimensional volume raw image of the test object by a non-destructive imaging testing method; and an image processing unit configured to:
identify regions of the three-dimensional volume raw image that are not to be attributed to the test object material by a threshold analysis of pixel values in the three-dimensional volume raw image, check an identified region of the three-dimensional volume raw image to determine whether it is completely embedded in regions that are to be associated with the test object material, assimilate the identified region of the three-dimensional volume raw image to the regions of the three-dimensional volume raw image that are to be associated with the test object material, when the identified region is determined to be completely embedded in regions that are to be associated with the test object material, thereby forming a filled three-dimensional volume raw image, and form a first flaw image by generating the difference between the three-dimensional volume raw image and the filled three-dimensional volume raw image.

12. The testing device according to claim 11, wherein the image processing unit is further configured to:
apply a filter algorithm to the three-dimensional volume raw image for amplifying possible flaw indicators, forming a filtered three-dimensional volume raw image, and limit value generation of the filtered three-dimensional volume raw image, forming a second three-dimensional flaw image.

13. The testing device according to claim 12, wherein the image processing unit is further configured to merge the first three-dimensional flaw image and the second three-dimensional flaw image into a combined three-dimensional flaw image.

14. The testing device according to claim 13, wherein the image processing unit is further configured to suppress in the combined three-dimensional flaw image the regions that are not to be associated with the test object material in the filled three-dimensional volume raw image.

15. The testing device according to claim 11, wherein the image processing unit is further configured to carry out a subtraction of the three-dimensional volume raw image in order to form the filtered three-dimensional volume raw image.

16. The testing device according to claim 11, wherein the image forming unit is further configured to form three-dimensional volume raw images of a test object by a tomography method based on X-radiation, ultrasound, or eddy currents.

17. The testing device according to claim 11, further comprising a classification unit configured to classify a test object on the basis of predefined test criteria.

18. The testing device according to claim 13, wherein the image processing unit is further configured to:
form a three-dimensional volume reference image from three-dimensional volume raw images of one or more test object(s) which was/were classified to be "In order" on the basis of predefined test criteria, and generate the difference between, on the one hand, the first three-dimensional flaw image, the second three-dimensional flaw image, or the combined three-dimensional flaw image and, on the other hand, the three-dimensional volume reference image.

19. The testing device according to claim 18, further comprising a registration unit configured to at least one of:
register a three-dimensional volume raw image to a three-dimensional volume reference image or to a 3D model of the test object, and register the three-dimensional volume reference image to a 3D model of the test object.

20. The method according to claim 2, wherein the filter algorithm is a cutoff filter or a median filter.

* * * * *